United States Patent
Kothandaraman et al.

(10) Patent No.: US 8,788,054 B2
(45) Date of Patent: Jul. 22, 2014

(54) SYSTEM AND METHOD FOR CONNECTING DEVICES TO A NEUROSTIMULATOR

(71) Applicant: Boston Scientific Neuromodulation Corporation, Valencia, CA (US)

(72) Inventors: Sridhar Kothandaraman, Valencia, CA (US); Mun Pook Lui, Northridge, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 13/971,784

(22) Filed: Aug. 20, 2013

(65) Prior Publication Data

US 2014/0067019 A1     Mar. 6, 2014

Related U.S. Application Data

(60) Provisional application No. 61/694,695, filed on Aug. 29, 2012.

(51) Int. Cl.
    *A61N 1/00*          (2006.01)

(52) U.S. Cl.
    USPC .......................................................... 607/60

(58) Field of Classification Search
    USPC .......................................................... 607/60
    See application file for complete search history.

(56) References Cited

U.S. PATENT DOCUMENTS

| 6,895,280 | B2 | 5/2005 | Meadows et al. |
|---|---|---|---|
| 2007/0150036 | A1 | 6/2007 | Anderson |
| 2007/0168004 | A1 | 7/2007 | Walter |
| 2007/0168007 | A1 | 7/2007 | Kuzma et al. |
| 2010/0010566 | A1 | 1/2010 | Thacker et al. |
| 2010/0121409 | A1 | 5/2010 | Kothandaraman et al. |
| 2011/0270065 | A1 * | 11/2011 | Ternes et al. .................. 600/373 |
| 2011/0282414 | A1 | 11/2011 | Kothandaraman et al. |

FOREIGN PATENT DOCUMENTS

WO    WO 2012158519     11/2012

OTHER PUBLICATIONS

PCT International Search Report for PCT/US2013/055884, Applicant: Boston Scientific Neuromodulation Corporation, Form PCT/ISA/210 and 220, dated Oct. 15, 2013 (5pages).
PCT Written Opinion of the International Search Authority for PCT/US2013/055884, Applicant: Boston Scientific Neuromodulation Corporation, Form PCT/ISA/237, dated Oct. 15, 2013 (6pages).

* cited by examiner

*Primary Examiner* — Robert N Wieland
(74) *Attorney, Agent, or Firm* — Vista IP Law Group LLP

(57) ABSTRACT

A method for defining connections between a plurality of lead bodies and a plurality of output ports of a neurostimulator, and an external control device for performing the method are disclosed. The external control device includes a user interface and control circuitry. The method includes displaying the lead bodies and the output ports of the neurostimulator; selecting a first one of the lead bodies; dragging a connector from the first lead body to a first one of the output ports of the neurostimulator; and dropping the connector onto the first output port of the neurostimulator, thereby defining a connection between the first lead body and the first output port of the neurostimulator. In another embodiment, a method includes defining the connection between the first lead body and the first output port, and graphically displaying the connection between the first lead body and the first output port of the neurostimulator.

16 Claims, 12 Drawing Sheets

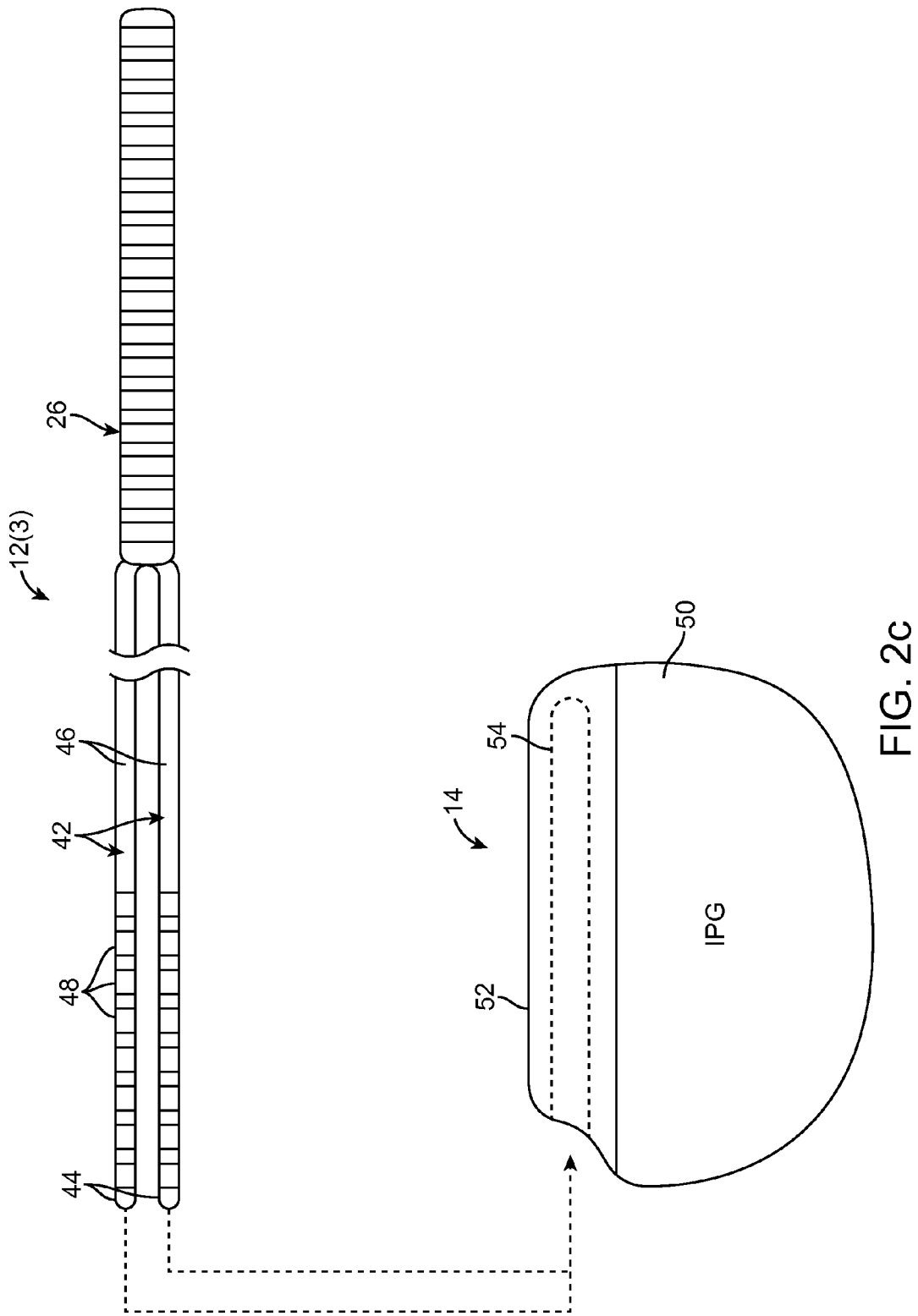

SYSTEM AND METHOD FOR CONNECTING DEVICES TO A NEUROSTIMULATOR

RELATED APPLICATION DATA

The present application claims the benefit under 35 U.S.C. §119 to U.S. provisional patent application Ser. No. 61/694,695, filed Aug. 29, 2012. The foregoing application is hereby incorporated by reference into the present application in its entirety.

FIELD OF THE INVENTION

The present invention relates to tissue stimulation systems, and more particularly, to a system and method for programming an implantable tissue stimulator.

BACKGROUND OF THE INVENTION

Implantable neurostimulation systems have proven therapeutic in a wide variety of diseases and disorders. Pacemakers and Implantable Cardiac Defibrillators (ICDs) have proven highly effective in the treatment of a number of cardiac conditions (e.g., arrhythmias). Spinal Cord Stimulation (SCS) systems have long been accepted as a therapeutic modality for the treatment of chronic pain syndromes, and the application of tissue stimulation has begun to expand to additional applications such as angina pectoralis and incontinence. Deep Brain Stimulation (DBS) has also been applied therapeutically for well over a decade for the treatment of refractory chronic pain syndromes, and DBS has also recently been applied in additional areas such as movement disorders and epilepsy. Further, in recent investigations Peripheral Nerve Stimulation (PNS) systems have demonstrated efficacy in the treatment of chronic pain syndromes and incontinence, and a number of additional applications are currently under investigation. Also, Functional Electrical Stimulation (FES) systems such as the Freehand system by NeuroControl (Cleveland, Ohio) have been applied to restore some functionality to paralyzed extremities in spinal cord injury patients.

These implantable neurostimulation systems typically include one or more electrode carrying neurostimulation leads, which are implanted at the desired stimulation site, and a neurostimulator (e.g., an implantable pulse generator (IPG)) implanted remotely from the stimulation site, but coupled either directly to the neurostimulation lead(s) or indirectly to the neurostimulation lead(s) via a lead extension. Thus, electrical pulses can be delivered from the neurostimulator to the neurostimulation leads to stimulate the tissue and provide the desired efficacious therapy to the patient. The neurostimulation system may further comprise a handheld patient programmer in the form of a remote control (RC) to remotely instruct the neurostimulator to generate electrical stimulation pulses in accordance with selected stimulation parameters. The RC may, itself, be programmed by a clinician, for example, by using a clinician's programmer (CP), which typically includes a general purpose computer, such as a laptop, with a programming software package installed thereon.

In the context of a SCS procedure, one or more neurostimulation leads are introduced through the patient's back into the epidural space, such that the electrodes carried by the leads are arranged in a desired pattern and spacing to create an electrode array. Multi-lead configurations have been increasingly used in electrical stimulation applications (e.g., neurostimulation, cardiac resynchronization therapy, etc.). In the neurostimulation application of SCS, the use of multiple leads increases the stimulation area and penetration depth (therefore coverage), as well as enables more combinations of anodic and cathodic electrodes for stimulation, such as transverse multipolar (bipolar, tripolar, or quadra-polar) stimulation, in addition to any longitudinal single lead configuration. After proper placement of the neurostimulation leads at the target area of the spinal cord, the leads are anchored in place at an exit site to prevent movement of the neurostimulation leads. To facilitate the location of the neurostimulator away from the exit point of the neurostimulation leads, lead extensions are sometimes used.

Each lead is then connected, either directly or indirectly through lead extensions, to one or more output ports in the IPG. The IPG can then be operated to generate electrical pulses that are delivered to the IPG output ports, through the leads and/or the lead extensions and conveyed through the lead electrodes to the targeted tissue within the spinal cord. If the connection between respective leads and respective output ports in the IPG is not correctly identified in the CP, it is possible that the patient will receive little or no benefit from an implanted SCS system, or that the programming performed by the CP will be very difficult and may take an extremely long time. Thus, correctly defining the connection between the leads and the ports of the IPG can reduce programming times, and can mean the difference between effective and ineffective pain therapy.

There, thus, remains a need to provide a user interface capable of allowing a user to easily define the connections between the leads and the ports of the IPG.

SUMMARY OF THE INVENTION

In accordance with one aspect of the present inventions, an external control device for selectively defining connections between a plurality of lead bodies, each coupled to at least one electrode, and a plurality of output ports of a neurostimulator is provided. The external control device includes a user interface configured for receiving input from a user, and for displaying the lead bodies and the output ports of the neurostimulator. The user interface may include a mouse, a trackball, a touchpad, and/or a joystick for receiving the input from the user. The user interface may include a digitizer screen for receiving the input from the user.

The external control device also includes control circuitry configured for, in response to input from the user, selecting a first one of the lead bodies, dragging a connector from the first lead body to a first one of the output ports of the neurostimulator, and dropping the connector onto the first output port of the neurostimulator, thereby defining a connection between the first lead body and the first output port of the neurostimulator. The user interface may be configured for displaying the connection between the first lead body and the first output port of the neurostimulator. The first lead body may include one of a plurality of tails of a lead. The first lead body may be a percutaneous lead.

The control circuitry may be further configured for verifying compatibility between the first lead body and the first output port of the neurostimulator. The control circuitry may be configured for selecting the first lead body by coupling a pointing device to the first lead body, configured for dragging the connector by moving the pointing device, and configured for dropping the connector by decoupling the pointing device from the dragged connector. The control circuitry may be further configured for, in response to additional input from the user, programming the neurostimulator with stimulation parameters corresponding to the at least one electrode to which the first lead body is coupled.

In an optional embodiment, the control circuitry is further configured for, in response to input from the user, selecting a second one of the lead bodies, dragging a second connector from the second lead body to a second one of the output ports of the neurostimulator, and dropping the second connector onto the second output port of the neurostimulator, thereby defining a connection between the second lead body and the second output port of the neurostimulator.

In accordance with another aspect of the present inventions, a method for selectively defining connections between a plurality of lead bodies, each coupled to at least one electrode, and a plurality of output ports of a neurostimulator is provided. The method includes displaying the lead bodies and the output ports of the neurostimulator, and selecting a first one of the lead bodies. The first lead body may include one of a plurality of tails of a lead. The first lead body may include a percutaneous lead.

The method further includes dragging a connector from the first lead body to a first one of the output ports of the neurostimulator, and dropping the connector onto the first output port of the neurostimulator, thereby defining a connection between the first lead body and the first output port of the neurostimulator. The method may further include verifying compatibility between the first lead body and the first output port of the neurostimulator. The method may further include programming the neurostimulator with stimulation parameters corresponding to the at least one electrode to which the first lead body is coupled.

In an optional embodiment, the method includes selecting a second one of the lead bodies; dragging a second connector from the second lead body to a second one of the output ports of the neurostimulator; and dropping the second connector onto the second output port of the neurostimulator, thereby defining a connection between the second lead body and the second output port of the neurostimulator.

In accordance with yet another aspect of the present inventions, an external control device for selectively displaying connections between a plurality of lead bodies, each coupled to at least one electrode, and a plurality of output ports of a neurostimulator is provided. The device includes control circuitry configured for, in response to input from a user, defining a connection between a first one of the lead bodies and a first one of the output ports of the neurostimulator. The first lead body may include one of a plurality of tails of a lead. The first lead body may be a percutaneous lead.

The control circuitry may be configured for defining the connection between the first lead body and the first output port of the neurostimulator by, in response to input from the user, selecting the first lead body, dragging a connector from the first lead body to the first output port of the neurostimulator, and dropping the connector onto the first output port of the neurostimulator. The control circuitry may be further configured for verifying compatibility between the first lead body and the first output port of the neurostimulator. The control circuitry may be further configured for, in response to additional input from the user, programming the neurostimulator with stimulation parameters corresponding to the at least one electrode to which the first lead body is coupled.

The device also includes a user interface configured for receiving input from the user, and for graphically displaying the lead bodies, the output ports of the neurostimulator, and the defined connection between the first lead body and the first output port of the neurostimulator. The user interface may include a mouse, a trackball, a touchpad, and/or a joystick for receiving the input from the user. The user interface may include a digitizer screen for receiving the input from the user.

In an optional embodiment, the control circuitry is further configured for, in response to additional input from the user, defining a connection between a second one of the lead bodies and a second one of the output ports of the neurostimulator, and the user interface is further configured for graphically displaying the connection between the second lead body and the second output port of the neurostimulator.

In accordance with still another embodiment of the present inventions, a method for selectively displaying connections between a plurality of lead bodies, each coupled to at least one electrode, and a plurality of output ports of a neurostimulator is provided. The method includes graphically displaying the lead bodies and the output ports of the neurostimulator, and defining a connection between a first one of the lead bodies and a first one of the output ports of the neurostimulator. The first lead body may include one of a plurality of tails of a lead. The first lead body may include a percutaneous lead. Defining the connection between the first lead body and the first output port of the neurostimulator may include selecting the first lead body; dragging a connector from the first lead body to the first output port of the neurostimulator; and dropping the connector onto the first output port of the neurostimulator.

The method further includes graphically displaying the defined connection between the first lead body and the first output port of the neurostimulator. The method may further include verifying compatibility between the first lead body and the first output port of the neurostimulator. The method may further include programming the neurostimulator with stimulation parameters corresponding to the at least one electrode to which the first lead body is coupled.

In an optional embodiment, the method includes defining a connection between a second one of the lead bodies and a second one of the output ports of the neurostimulator; and graphically displaying the defined connection between the second lead body and the second output port of the neurostimulator.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which:

FIG. 2c is a plan view of an IPG and another embodiment of a percutaneous stimulation lead used in the SCS system of FIG. 1;

DETAILED DESCRIPTION OF THE EMBODIMENTS

The description that follows relates to a spinal cord stimulation (SCS) system. However, it is to be understood that while the invention lends itself well to applications in SCS, the invention, in its broadest aspects, may not be so limited. Rather, the invention may be used with any type of implantable electrical circuitry used to stimulate tissue. For example, the present invention may be used as part of a pacemaker, a defibrillator, a cochlear stimulator, a retinal stimulator, a stimulator configured to produce coordinated limb movement, a cortical stimulator, a deep brain stimulator, peripheral nerve stimulator, microstimulator, or in any other neural stimulator configured to treat urinary incontinence, sleep apnea, shoulder sublaxation, headache, etc.

Figure 1:
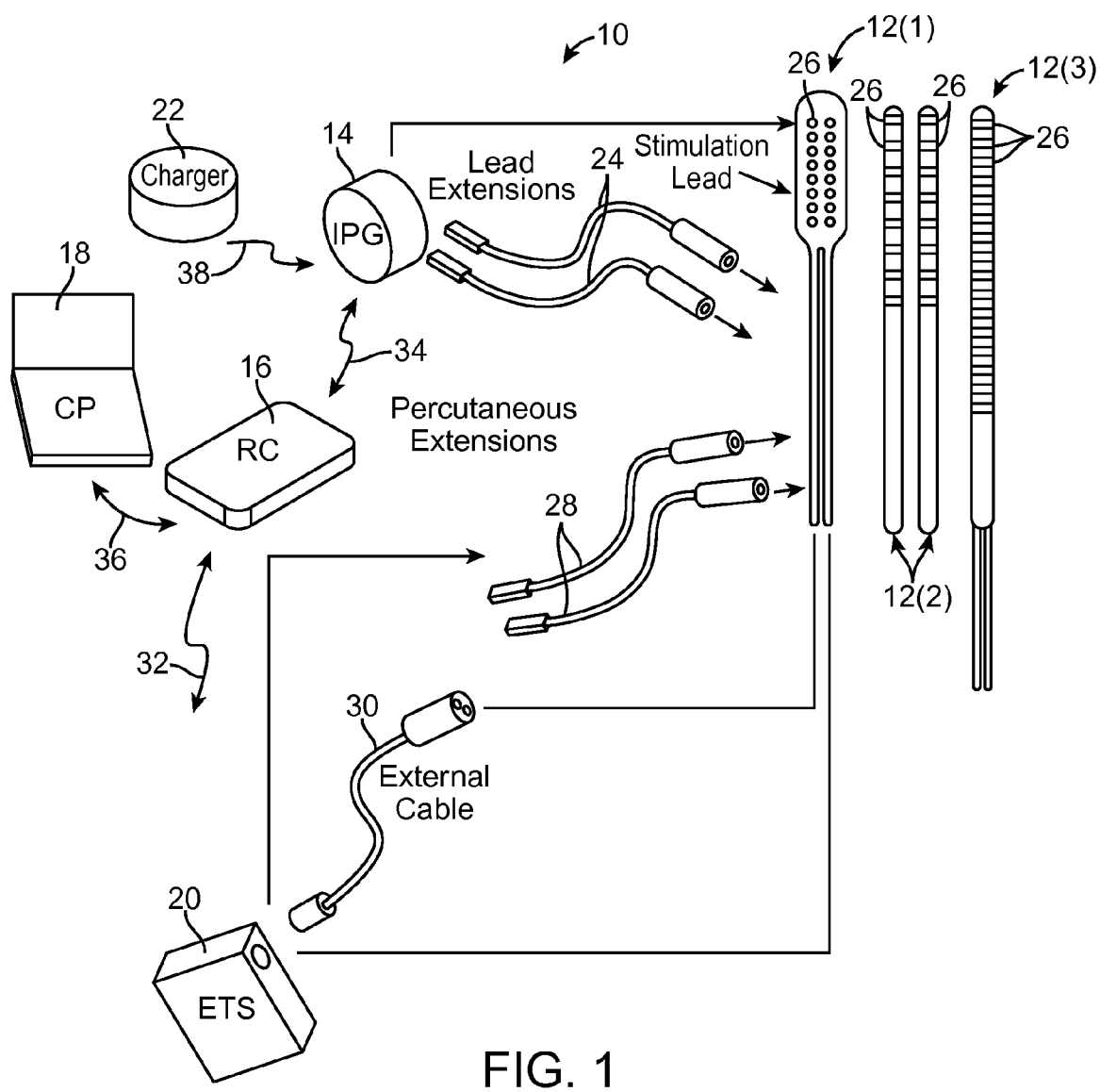
FIG. 1 is plan view of one embodiment of a spinal cord stimulation (SCS) system arranged in accordance with the present inventions.

Turning first to FIG. 1, an exemplary SCS system 10 generally comprises at least one implantable stimulation lead 12 (e.g., a surgical paddle lead 12(1), multiple percutaneous leads 12(2) having eight electrodes, and/or a percutaneous lead having sixteen electrodes 12(3)), an implantable pulse generator (IPG) 14, an external remote control (RC) 16, a Clinician's Programmer (CP) 18, an External Trial Stimulator (ETS) 20, and an external charger 22.

The IPG 14 is physically connected via lead extensions 24 to the stimulation lead(s) 12, which carries a plurality of electrodes 26 arranged in an array. In the illustrated embodiment, the surgical paddle lead 12(1) carries two columns of electrodes 26, the percutaneous leads 12(2) respectively carry two columns of electrodes 26, and the percutaneous lead 12(3) carries one column of sixteen electrodes 26. Two lead extensions 24 are used to physically connect the IPG 14 to the stimulation lead(s) 12. As will be described in further detail below, the IPG 14 includes pulse generation circuitry that delivers electrical stimulation energy in the form of a pulsed electrical waveform (i.e., a temporal series of electrical pulses) to the electrode array 26 in accordance with a set of stimulation parameters.

The ETS 20 may also be physically connected via percutaneous lead extensions 28 and/or an external cable 30 to the stimulation lead 12. The ETS 20, which has pulse generation circuitry similar to that of the IPG 14, also delivers electrical stimulation energy in the form of a pulse electrical waveform to the electrode array 26 accordance with a set of stimulation parameters. The major difference between the ETS 20 and the IPG 14 is that the ETS 20 is a non-implantable device that is used on a trial basis after the stimulation lead 12 has been implanted and prior to implantation of the IPG 14, to test the responsiveness of the stimulation that is to be provided. Thus, any functions described herein with respect to the IPG 14 can likewise be performed with respect to the ETS 20. Further details of an exemplary ETS are described in U.S. Pat. No. 6,895,280, which is expressly incorporated herein by reference.

The RC 16 may be used to telemetrically control the ETS 20 via a bi-directional RF communications link 32. Once the IPG 14 and stimulation lead 12 are implanted, the RC 16 may be used to telemetrically control the IPG 14 via a bi-directional RF communications link 34. Such control allows the IPG 14 to be turned on or off and to be programmed with different stimulation programs after implantation.

The CP 18 provides clinician detailed stimulation parameters for programming the IPG 14 and ETS 20 in the operating room and in follow-up sessions. The CP 18 may perform this function by indirectly communicating with the IPG 14 or ETS 20, through the RC 16, via an IR communications link 36. Alternatively, the CP 18 may directly communicate with the IPG 14 or ETS 20 via an RF communications link (not shown).

The external charger 22 is a portable device used to transcutaneously charge the IPG 14 via an inductive link 38. For purposes of brevity, the details of the external charger 22 will not be described herein. Details of exemplary embodiments of external chargers are disclosed in U.S. Pat. No. 6,895,280, which has been previously incorporated herein by reference. Once the IPG 14 has been programmed, and its power source has been charged by the external charger 22 or otherwise replenished, the IPG 14 may function as programmed without the RC 16 or CP 18 being present.

As briefly discussed above, one of the stimulation leads may be a surgical paddle lead 12(1). To this end, and with reference to FIG. 2a, the surgical paddle lead 12(1) comprises a paddle-shaped membrane 40, and two elongated tails, or lead bodies 42, extending from the paddle-shaped membrane 40. Each of the lead bodies 42 has a proximal end 44 and a distal end 46. Each lead body 42 may, e.g., have a diameter within the range of 0.03 inches to 0.07 inches and a length within the range of 30 cm to 90 cm for spinal cord stimulation applications. Each lead body 42 may be composed of a suitable electrically insulative and biocompatible material, such as a polymer (e.g., polyurethane or silicone), and may be extruded as a unibody construction. The paddle-shaped membrane 40 is composed of an electrically insulative and biocompatible material, such as silicone.

The surgical paddle lead 12(1) further comprises proximal contacts 48 mounted to the proximal ends 44 of the lead bodies 42 and the plurality of electrodes 26 mounted on one side of the paddle-shaped membrane 40 in a two-dimensional arrangement. Eight proximal contacts 48 are mounted to the proximal end 44 of each of the lead bodies 42. The electrodes 26 are in a 2×8 arrangement with two columns having eight electrodes 26 in each column. Although the stimulation lead 12(1) is shown as having sixteen electrodes 26 (and thus, sixteen corresponding proximal contacts 48 on the lead bodies 42), the number of electrodes may be any number suitable for the application in which the surgical paddle lead 12(1) is intended to be used.

Instead of two lead bodies 42, the surgical paddle lead 12(1) may alternatively have three or four lead bodies. For example, a 4×8 surgical paddle lead (not shown) comprises four columns of electrodes with eight electrodes in each column, and four lead bodies. The system 10 shown in FIG. 1 may be modified to accommodate a 4×8 surgical paddle lead by adding two more lead extensions 24 and/or two more percutaneous extensions 28 to the system 10. Similarly, if a surgical paddle lead having three lead bodies is used in the system 10, three lead extensions would be needed for the system 10.

Figure 2A:
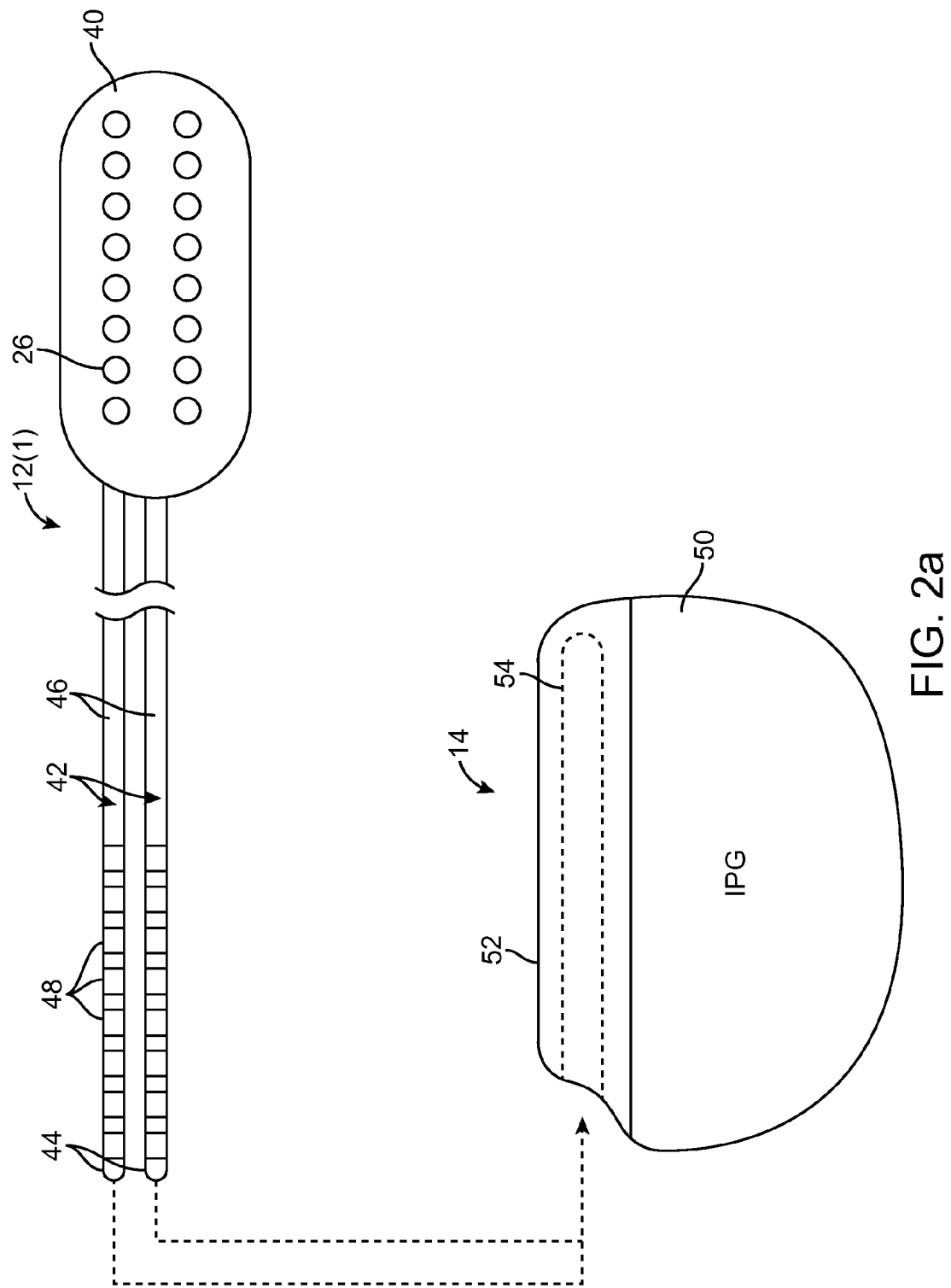
FIG. 2a is a plan view of an implantable pulse generator (IPG) and one embodiment of a surgical paddle stimulation lead used in the SCS system of FIG. 1.

Each of the electrodes 26 in the surgical paddle lead 12(1) illustrated in FIG. 2a takes the form of a disk composed of an electrically conductive, non-corrosive, material, such as, e.g., platinum, titanium, stainless steel, or alloys thereof. Each of the proximal contacts 48 in the surgical paddle lead 12(1) illustrated in FIG. 2a takes the form of a cylindrical ring element composed of an electrically conductive, biocompatible, non-corrosive, material, such as, e.g., platinum, titanium, stainless steel, or alloys thereof.

The surgical paddle lead 12(1) also includes a plurality of electrical conductors (not shown) extending through individual lumens (not shown) within each lead body 42 and connected between the respective proximal contacts 48 and electrodes 26 using suitable means, such as welding. Further details regarding the construction and method of manufacture of surgical paddle leads are disclosed in U.S. Patent Application Publication No. 2007/0150036, entitled "Stimulator Leads and Methods for Lead Fabrication," the disclosure of which is expressly incorporated herein by reference.

As briefly discussed above, instead of a surgical paddle lead 12(1), two percutaneous leads 12(2) having eight electrodes 26 each may be used. To this end, and with reference to FIG. 2b, each percutaneous lead 12(2) comprises an elongated lead body 42 having a proximal end 44 and a distal end 46. Each lead body 42 may, e.g., have a diameter within the range of 0.03 inches to 0.07 inches and a length within the range of 30 cm to 90 cm for spinal cord stimulation applications. The lead body 42 may be composed of a suitable electrically insulative and biocompatible material, such as, a polymer (e.g., polyurethane or silicone), and may be extruded as a unibody construction.

Each percutaneous lead 12(2) further comprises a plurality of proximal contacts 48 mounted to the proximal end 44 of the lead body 42 and the plurality of in-line electrodes 26 mounted to the distal end 46 of the lead body 42. Although each of the percutaneous leads 12(2) is shown as having eight electrodes 26 (and thus, eight corresponding proximal contacts 48), the number of electrodes may be any number suitable for the application in which the percutaneous lead 12(2) is intended to be used (e.g., one, two, four, sixteen, etc.). Similarly, although the system 10 is depicted as accommodating four percutaneous leads, the number of leads may be any number suitable for the application in which the system 10 is intended to be used.

As briefly discussed above, a percutaneous lead 12(3) having sixteen electrodes 26 and two tails, or lead bodies 42, as shown in FIG. 2c may be used in the system 10. Each of the lead bodies 42 includes eight proximal contacts 48 mounted to the proximal end thereof. The proximal contacts 48 on one of the lead bodies 42 correspond to the distal set of eight electrodes on the lead 12(2), and the proximal contacts 48 on the other lead body 42 correspond to the proximal set of eight electrodes.

Figure 2B:
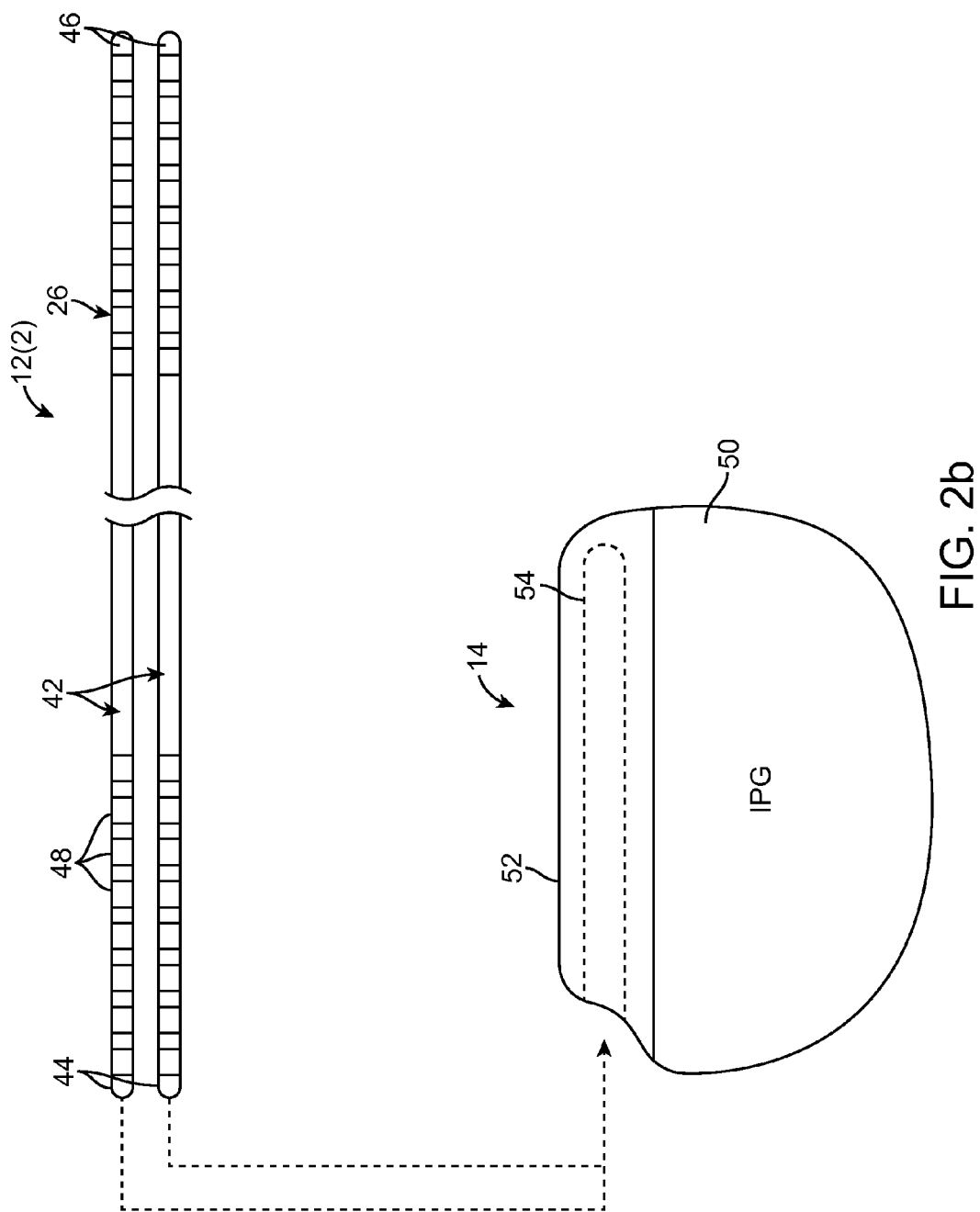
FIG. 2b is a plan view of an IPG and one embodiment of a percutaneous stimulation lead used in the SCS system of FIG. 1.

Each of the electrodes 26 and proximal contacts 48 in the percutaneous leads 12(2) and 12(3) illustrated in FIGS. 2b and 2c takes the form of a cylindrical ring element composed of an electrically conductive, biocompatible, non-corrosive, material, such as, e.g., platinum, titanium, stainless steel, or alloys thereof, which is circumferentially disposed about the lead bodies 42.

Each percutaneous lead 12(2) and 12(3) also includes a plurality of electrical conductors (not shown) extending within the lead body 42 and connected between the respective proximal contacts 48 and electrodes 26 using suitable means, such as welding. Further details describing the construction and method of manufacturing percutaneous stimulation leads are disclosed in U.S. Patent Application Publication No. 2007/0168007, entitled "Lead Assembly and Method of Making Same," and U.S. Patent Application Publication No. 2007/0168004, entitled "Cylindrical Multi-Contact Electrode Lead for Neural Stimulation and Method of Making Same," the disclosures of which are expressly incorporated herein by reference.

Referring to any of FIG. 2a, 2b, or 2c, the IPG 14 comprises an outer case 50 housing the electronic and other components (described in further detail below). The outer case 50 is composed of an electrically conductive, biocompatible material, such as titanium, and forms a hermetically sealed compartment wherein the internal electronics are protected from the body tissue and fluids. In some cases, the outer case 50 serves as an electrode. The IPG 14 further comprises a connector 52 in which the proximal ends 44 of the lead bodies 42 of the stimulation leads 12 can mate in a manner that electrically couples the electrodes 26 to the electronics contained within the outer case 50. To this end, the connector 52 includes a four ports 54 (only one shown in phantom) for receiving the proximal ends 44 of the two lead bodies 42 of the surgical paddle lead 12(1), or the proximal ends 44 of the two bodies 42 of the respective percutaneous leads 12(2), or the proximal ends 44 of the two lead bodies of the percutaneous lead 12(3). In the case where the lead extensions 24 are used, the ports 54 may instead receive the proximal ends of such lead extensions 24.

It should be noted that, although the lead bodies of the surgical paddle lead 12(1) or the percutaneous leads 12(2) or 12(3) will be described hereinafter as being mated with the ports 54, lead extensions, adaptors, and/or splitters can be considered to be lead bodies when mated with the respective surgical paddle lead or percutaneous leads. Thus, for the purposes of this specification, a "lead body" is simply an elongated member with proximal contacts that can be mated to a port of a neurostimulator to allow the electrodes on the surgical paddle lead or percutaneous lead to be electrically coupled to the circuitry contained within the neurostimulator. The significance for the present inventions is that the connection between each of the lead bodies (which may include a lead extension, adaptor, and/or splitter) and the port 54 in the IPG 14 can be defined in the CP 18 so that the CP 18 can properly program the IPG 14 to provide the correct stimulation parameters to the correct electrodes at the distal ends of the lead bodies.

As will be described in further detail below, the IPG 14 includes pulse generation circuitry that provides electrical stimulation energy to the electrodes 26 in accordance with a set of parameters. Such parameters may comprise electrode combinations, which define the electrodes that are activated as anodes (positive), cathodes (negative), and turned off (zero), and electrical pulse parameters, which define the pulse amplitude (measured in milliamps or volts depending on whether the IPG 14 supplies constant current or constant voltage to the electrodes), pulse duration (measured in microseconds), pulse rate (measured in pulses per second), and pulse shape.

With respect to the pulse patterns provided during operation of the SCS system 10, electrodes that are selected to transmit or receive electrical energy are referred to herein as "activated," while electrodes that are not selected to transmit or receive electrical energy are referred to herein as "non-activated." Electrical energy delivery will occur between two (or more) electrodes, one of which may be the IPG case 50, so that the electrical current has a path from the energy source contained within the IPG case 50 to the tissue and a sink path from the tissue to the energy source contained within the case. Electrical energy may be transmitted to the tissue in a monopolar or multipolar (e.g., bipolar, tripolar, etc.) fashion.

Monopolar delivery occurs when a selected one or more of the lead electrodes 26 is activated along with the case 50 of the IPG 14, so that electrical energy is transmitted between the selected electrode 26 and case 50. Monopolar delivery may also occur when one or more of the lead electrodes 26 are activated along with a large group of lead electrodes located remotely from the one or more lead electrodes 26 so as to create a monopolar effect; that is, electrical energy is conveyed from the one or more lead electrodes 26 in a relatively isotropic manner. Bipolar delivery occurs when two of the lead electrodes 26 are activated as anode and cathode, so that electrical energy is transmitted between the selected electrodes 26. Tripolar delivery occurs when three of the lead electrodes 26 are activated, two as anodes and the remaining one as a cathode, or two as cathodes and the remaining one as an anode.

Figure 3:
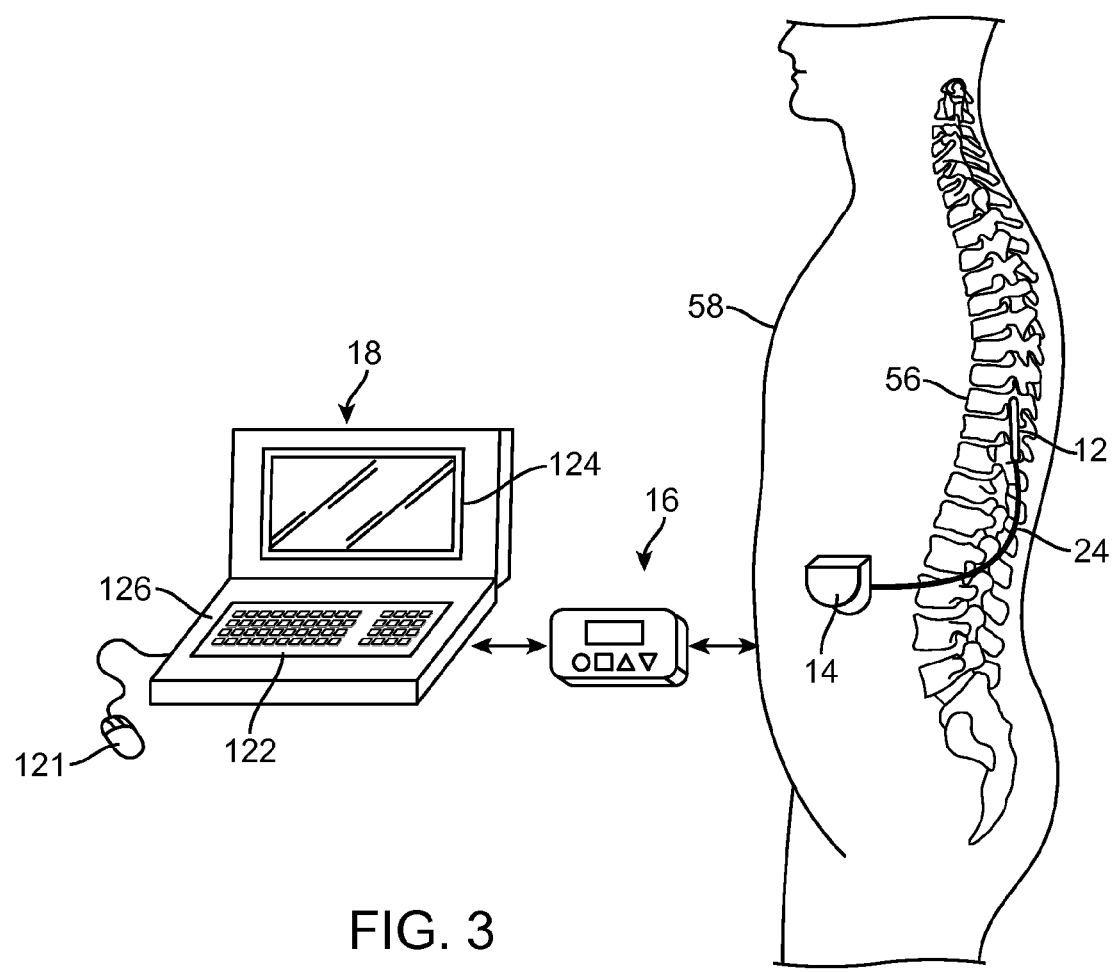
FIG. 3 is a plan view of the SCS system of FIG. 1 in use with a patient.

Referring to FIG. 3, the stimulation lead 12 (either 12(1), 12(2), or 12(3)) is implanted within the spinal column 56 of a patient 58. The preferred placement of the electrode leads 12 is adjacent, i.e., resting near, or upon the dura, adjacent to the spinal cord area to be stimulated. While the electrode lead 12 is illustrated as being implanted near the spinal cord area of a patient, the electrodes lead 12 may be implanted anywhere in the patient's body, including a peripheral region, such as a limb, or the brain. Due to the lack of space near the location where the electrode lead 12 exits the spinal column 56, the IPG 14 is generally implanted in a surgically-made pocket either in the abdomen or above the buttocks. The IPG 14 may, of course, also be implanted in other locations of the patient's body. The lead extensions 24 facilitate locating the IPG 14 away from the exit point of the electrode lead 12. As there shown, the CP 18 communicates with the IPG 14 via the RC 16.

As briefly discussed above, the CP 18 greatly simplifies the programming of multiple electrode combinations, allowing the user (e.g., the physician or clinician) to readily determine the desired stimulation parameters to be programmed into the IPG 14, as well as the RC 16. Thus, modification of the stimulation parameters in the programmable memory of the IPG 14 after implantation is performed by a user using the CP 18, which can directly communicate with the IPG 14 or indirectly communicate with the IPG 14 via the RC 16. That is, the CP 18 can be used by the user to modify operating parameters of the electrode array 26 near the spinal cord.

As shown in FIG. 3, the overall appearance of the CP 18 is that of a laptop personal computer (PC), and in fact, may be implemented using a PC that has been appropriately configured to include a directional-programming device and programmed to perform the functions described herein. Thus, the programming methodologies can be performed by executing software instructions contained within the CP 18. Alternatively, such programming methodologies can be performed using firmware or hardware. In any event, the CP 18 may actively control the characteristics of the electrical stimulation generated by the IPG 14 to allow the optimum stimulation parameters to be determined based on patient feedback and may subsequently program the IPG 14 with the optimum stimulation parameters.

To allow the clinician to perform these functions, the CP 18 includes a user interface. In the illustrated embodiment, the user interface of the CP 18 includes a mouse 121, a keyboard 122, and a programming display screen 124 housed in a case 126. It is to be understood that in addition to, or in lieu of, the mouse 121, other directional programming devices may be used, such as a trackball, touchpad, joystick, or directional keys included as part of the keys associated with the keyboard 122.

In the illustrated embodiment described below, the display screen 124 takes the form of a conventional screen, in which case, a virtual pointing device, such as a cursor controlled by a mouse, joy stick, trackball, etc, can be used to manipulate graphical objects on the display screen 124. In alternative embodiments, the display screen 124 takes the form of a digitizer touch screen, which may be either passive or active. If passive, the display screen 124 includes detection circuitry that recognizes pressure or a change in an electrical current when a passive device, such as a finger or non-electronic stylus, contacts the screen. If active, the display screen 124 includes detection circuitry that recognizes a signal transmitted by an electronic pen or stylus. In either case, detection circuitry is capable of detecting when a physical pointing device (e.g., a finger, a non-electronic stylus, or an electronic stylus) is in close proximity to the screen 124, whether it be making physical contact between the pointing device and the screen or bringing the pointing device in proximity to the screen within a predetermined distance, as well as detecting the location of the screen in which the physical pointing device is in close proximity. When the pointing device touches or otherwise is in close proximity to the screen, the graphical object on the screen adjacent to the touch point is "locked" for manipulation, and when the pointing device is moved away from the screen the previously locked object is unlocked.

Figure 4:
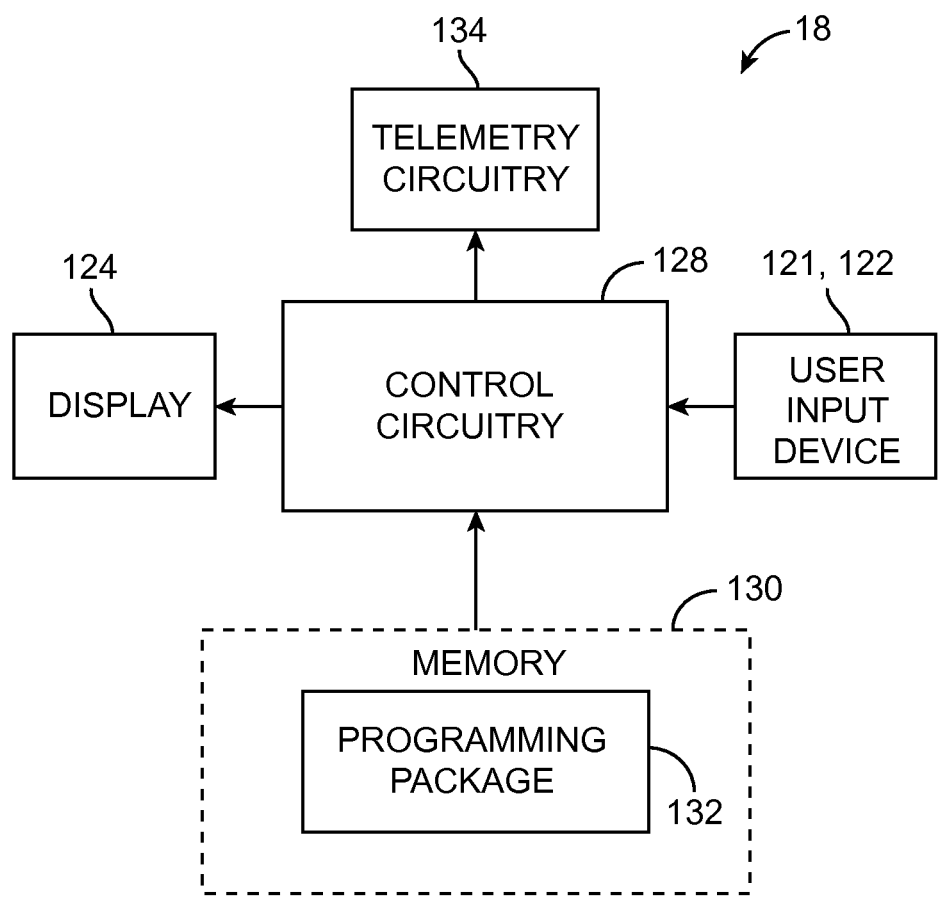
FIG. 4 is a block diagram of the components of a clinician's programmer that can be used in the SCS system of FIG. 1.

As shown in FIG. 4, the CP 18 generally includes control circuitry 128 (e.g., a central processor unit (CPU)) and memory 130 that stores a stimulation programming package 132, which can be executed by the control circuitry 128 to allow a clinician to program the IPG 14 and RC 16. The control circuitry 128 is in communication with a user input device, which in the illustrated embodiment includes the mouse 121 and the keyboard 122, but may, as discussed above, alternatively or additionally include other devices. The CP 18 further includes telemetry circuitry 134 for downloading stimulation parameters to the RC 16 and uploading stimulation parameters already stored in the memory of the RC 16 via link 36 (shown in FIG. 1). The telemetry circuitry 134 is also configured for transmitting the control data (including stimulation parameters and requests to provide status information) to the IPG 14 and receiving status information (including the measured electrical data) from the IPG 14 indirectly via the RC 16.

Execution of the programming package 132 by the control circuitry 128 provides a multitude of display screens (not shown) that can be navigated through via use of the mouse 121. These display screens allow the clinician to, among other functions, select or enter patient profile information (e.g., name, birth date, patient identification, physician, diagnosis, and address), enter procedure information (e.g., programming/follow-up, implant trial system, implant IPG, implant IPG and lead(s), replace IPG, replace IPG and leads, replace or revise leads, explant, etc.), generate a pain map of the patient, define the configuration and orientation of the leads, initiate and control the electrical stimulation energy output by the neurostimulation leads 12, and select and program the IPG 14 with stimulation parameters in both a surgical setting and a clinical setting. Further details discussing the above-described CP functions are disclosed in U.S. Patent Application Publication No. 2010/0010566, entitled "System and Method for Converting Tissue Stimulation Programs in a Format Usable by an Electrical Current Steering Navigator," and U.S. Patent Application Publication No. 2010/0121409, entitled "System and Method for Determining Appropriate Steering Tables for Distributing Stimulation Energy Among Multiple Neurostimulation Electrodes," which are expressly incorporated herein by reference.

Most pertinent to the present inventions, programming of the IPG 14 can be performed based on a user-defined connection between a lead body and an output port of the IPG corresponding to the actual physical connection between the lead body 42 and the output port 54 of the IPG 14. This connection is graphically displayed along with a graphical depiction of the lead body and a graphical depiction of a plurality of output ports of the IPG.

Figure 5B:
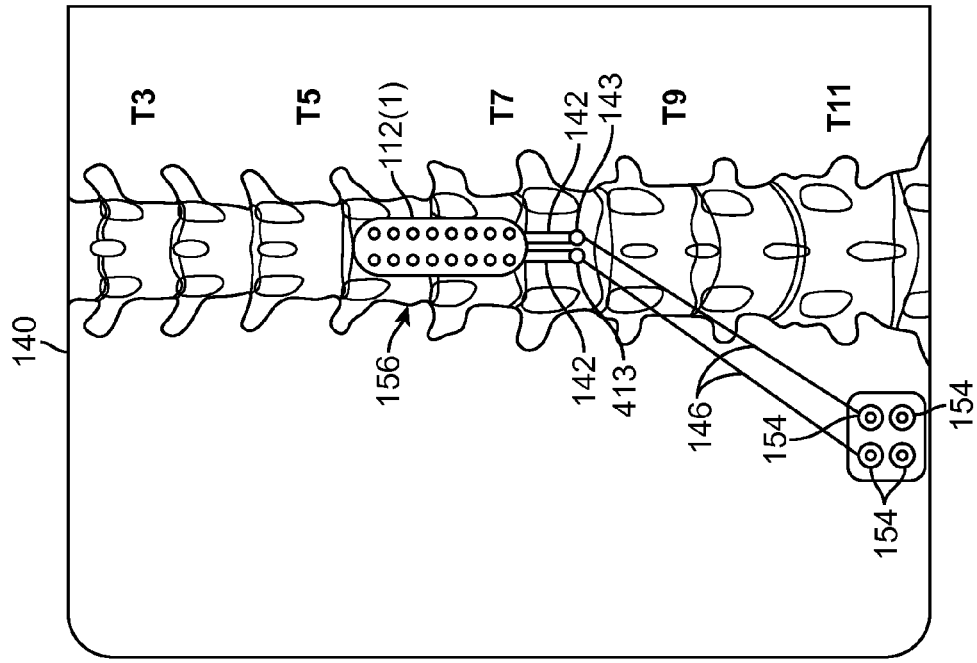
FIGS. 5a through 10b are illustrations of programming screens that can be displayed by the clinician programmer of FIG. 4, and used to define a connection between a lead body and an output port of the IPG.
Figure 5A:
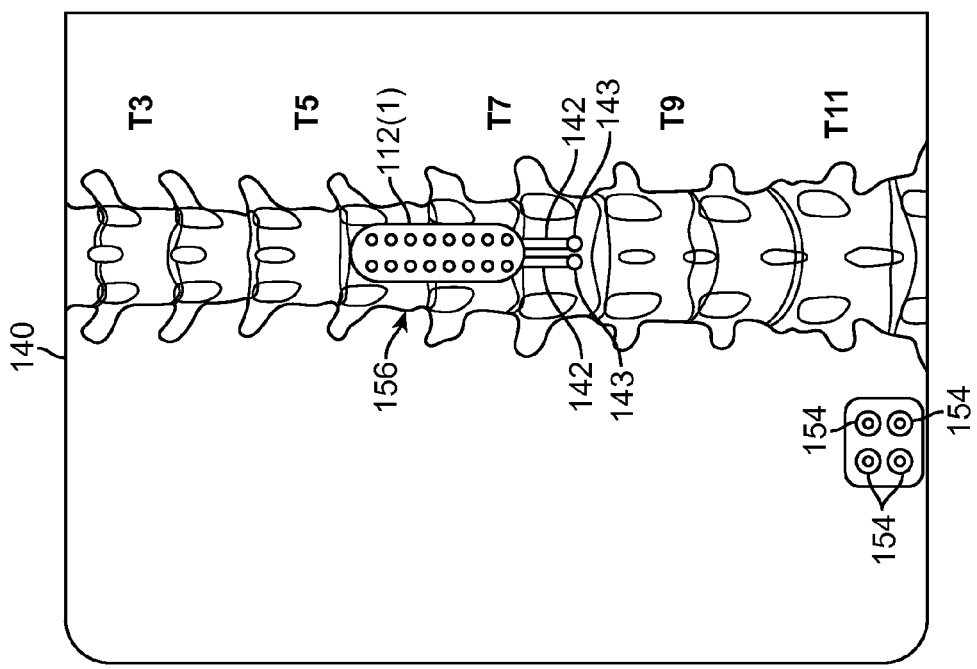

The connection may be defined using the programming screen 140 shown in FIGS. 5*a*-7*b*. Before the connection is defined, the programming screen 140 displays lead bodies 142, connectors 143 at the ends of the lead bodies 142, and a plurality of output ports 154 of the IPG. The lead bodies 142 may be graphically displayed in the context of an anatomical region, and in this case, the spinal column 156 of the patient. The lead bodies 142 shown in FIG. 5*a* are tails of a surgical paddle lead 112(1), the lead bodies 142 shown in FIG. 6*a* are percutaneous leads 112(2), and the lead bodies 142 shown in FIG. 7*a* are tails of a percutaneous lead 112(3). Although the screen 140 is shown displaying two lead bodies, the number of lead bodies displayed may be any number corresponding to the number of lead bodies that are implanted within the patient.

Figure 6B:
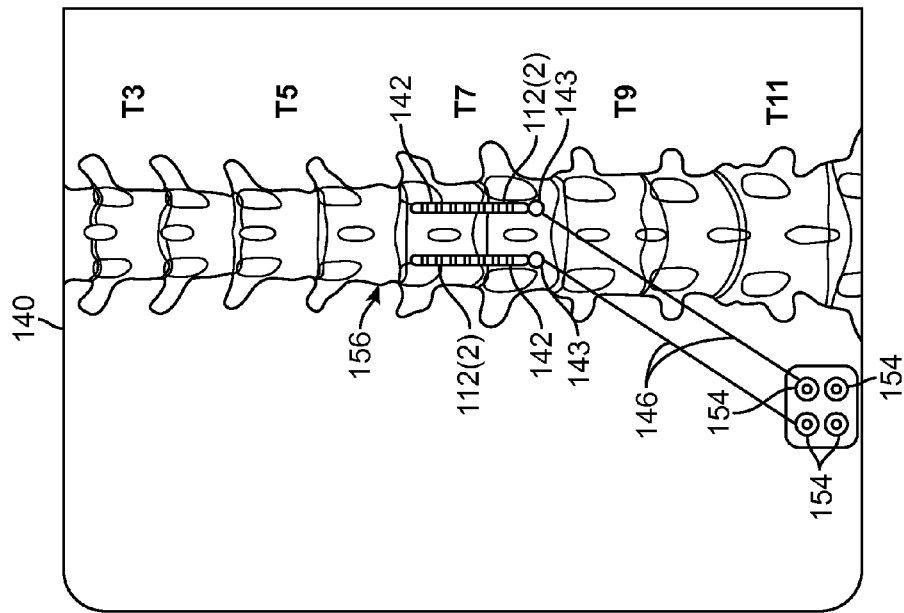
Figure 6A:
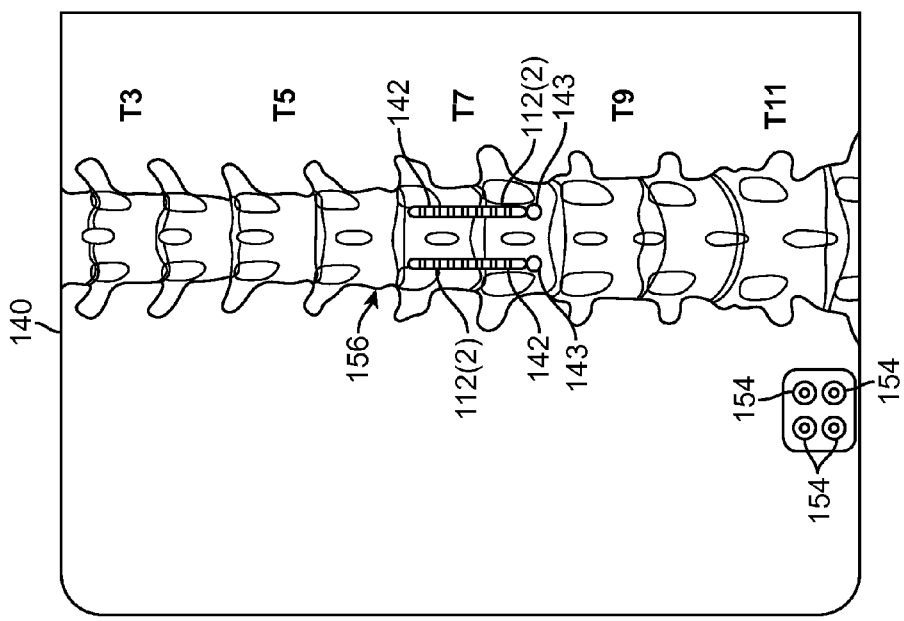
Figure 7B:
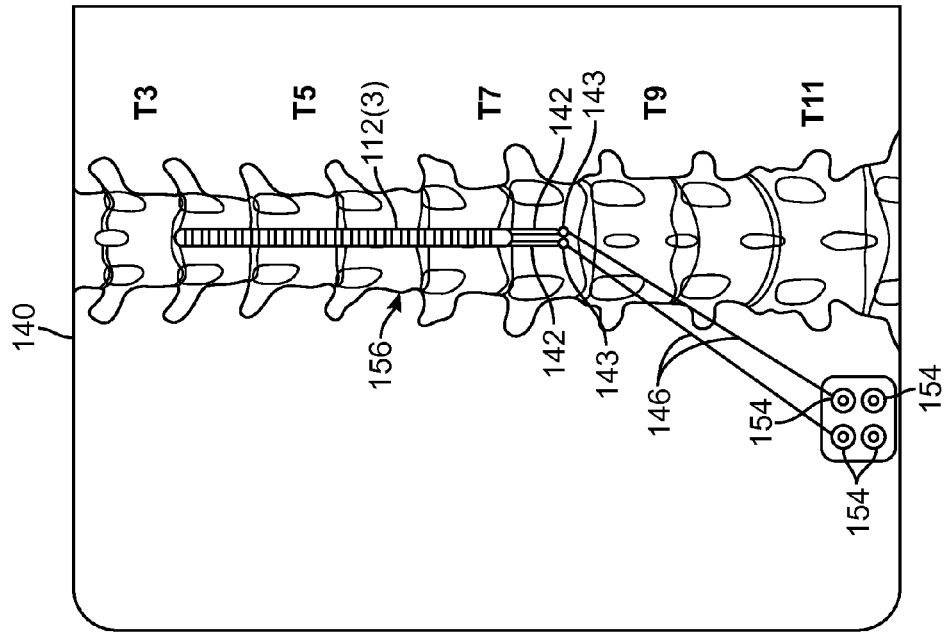
Figure 7A:
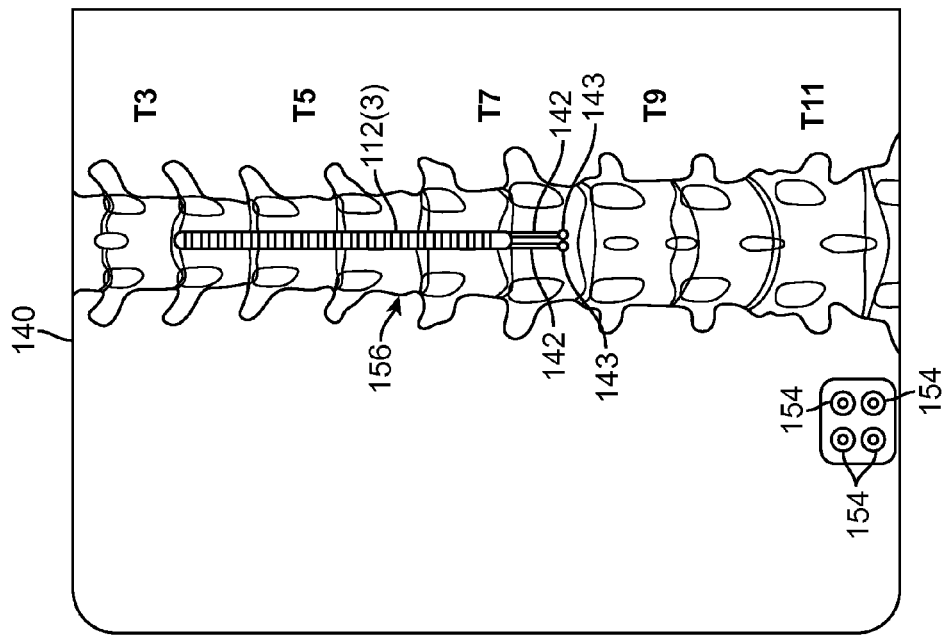

The connection between one of the lead bodies 142 and one of the output ports 154 is defined by first selecting the lead body 142. If the lead body 142 is one of the tails of a surgical paddle lead 112(1) as shown in FIG. 5*a*, then the lead body 142 is selected by selecting one of the plurality of tails of the surgical paddle lead 112(1). If the lead body 142 is a percutaneous lead 112(2), as shown in FIG. 6*a*, then the lead body 142 is selected by selecting the percutaneous lead 112(2). If the lead body 142 is one the tails of a percutaneous lead 112(3), as shown in FIG. 7*a*, then the lead body 142 is selected by selecting one of the plurality of tails. When the lead body 142 is selected, a lead body connector 143 appears. Alternatively, rather than selecting the lead body, the lead body connector 143 may be selected. The lead body connector 143 is capable of being displaced relative to the lead body 142. After selecting the lead body 142, the connector 143 is dragged from the lead body 142 to one of the output ports 154, and then dropped onto the output port 154. The control circuitry is configured for verifying compatibility between the lead body 142 and the output port 154 of the IPG. The procedure is then repeated for defining a connection between the other lead body 142 and another output port 154 of the IPG. If compatibility is verified, then the defined connections 146 are displayed as shown in FIGS. 5*b*, 6*b*, and 7*b*. The defined connections 146 are then used during programming the IPG 14 so that the stimulation is directed to the correct electrodes.

The manner in which the lead body 142 is selected, and the lead body connector 143 is dragged and dropped will depend on the nature of the user interface. For example, if the display screen 124 is conventional, and a mouse 121 is used to control a pointing device, such as a cursor, the user may couple the cursor to the lead body 142 by, e.g., placing the cursor adjacent to the lead body 142 and clicking and holding on the appropriate button of the mouse 121, thereby selecting the lead body 142. The user can then move the cursor to displace the lead body connector 143 within the programming screen 140, thereby dragging the lead body connector 143 towards the selected IPG output port 154. Once the lead body connector 143 is within the selected IPG output port 154, the user can release the button of the mouse 121 to decouple the cursor from the lead body connector 143, thereby dropping the lead body connector within the selected IPG output port 154.

As another example, if the display screen 124 is a digitizer screen, and a stylus or finger is used as the pointing device, the user may couple the stylus/finger to the lead body 142 by, e.g., placing the stylus/finger adjacent to the lead body 142 and physically touching the programming screen, thereby selecting the lead body 142. The user can then move the stylus/finger across the programming screen 140 to displace a lead body connector 143 within the screen, thereby dragging the lead body connector 143 toward the selected IPG output port 154. Once the lead body connector 143 is within the selected IPG output port 154, the user can remove the stylus/finger from the programming screen 140 to decouple the stylus/finger from the lead body connector 143, thereby dropping the lead body connector 143 into the IPG output port 154.

As briefly mentioned above, the connection between a lead and an output port of the IPG may include lead extensions, adaptors, and/or splitters. FIGS. 8*a*-10*b* depict exemplary programming screens 140 for defining a connection between a lead and an output port that includes an adaptor or a splitter.

Figure 8B:
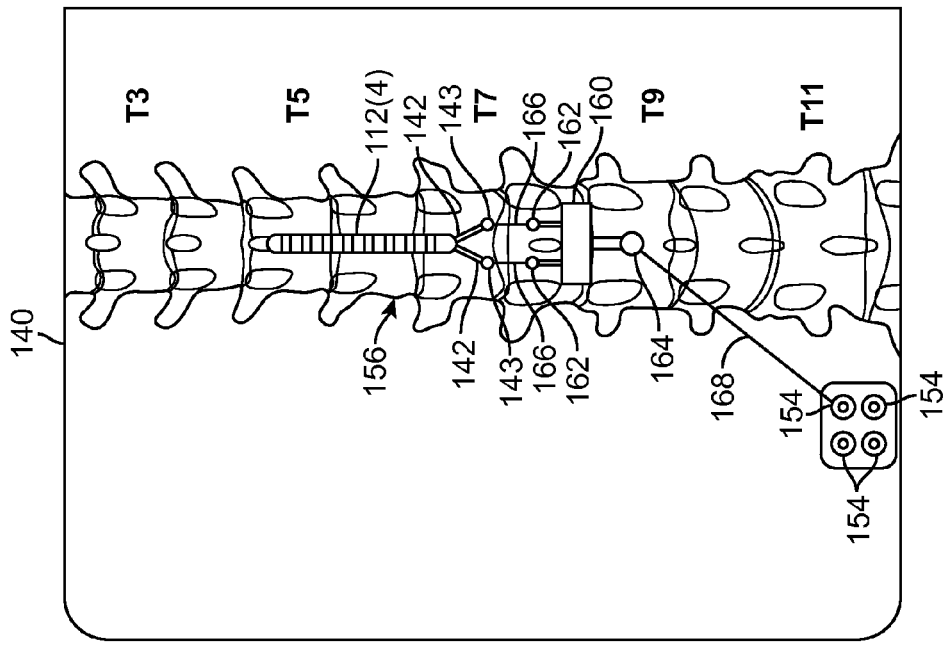
Figure 8A:
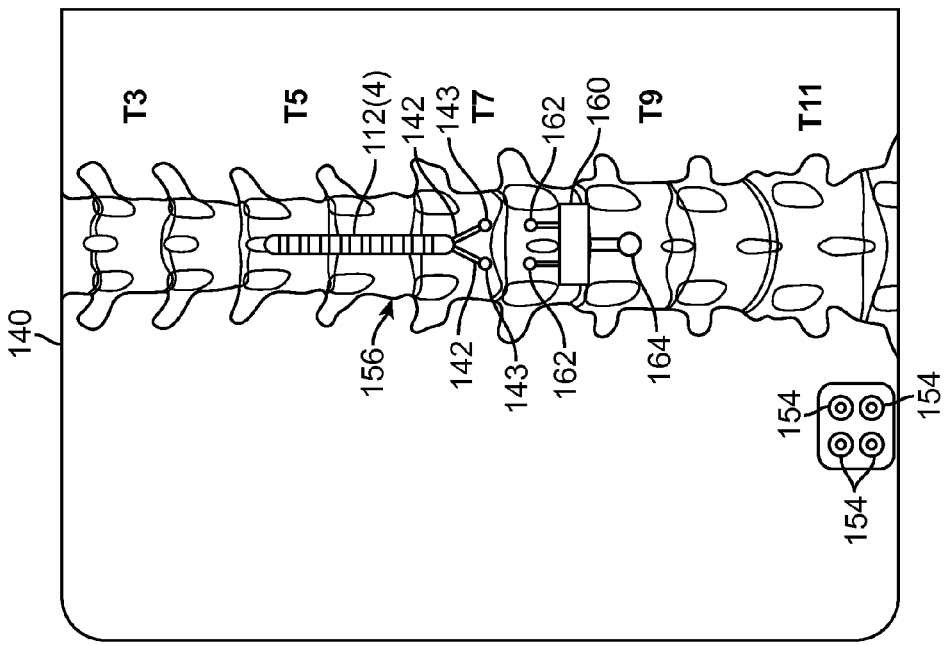

FIG. 8*a* depicts a lead 112(4) having eight electrodes and two tails, or lead bodies 142. Each lead body 142 includes a connector 143 coupled to four of the electrodes. An adaptor 160 is depicted in FIG. 8*a* as being disposed between the lead bodies 142 and the output ports 154 of the IPG. The side of the adaptor 160 facing the lead bodies 142 includes two distal connectors 162 configured for being coupled to the lead body connectors 143. The side of the adaptor 160 facing the output ports 154 of the IPG includes one proximal connector 164 configured for being coupled to one of the output ports 154 of the IPG. In this manner, the adaptor 160 is configured for coupling both of the lead bodies 142 to a single one of the output ports 154. In a method for defining the connection between the lead bodies 142 and one of the output ports 154, one of the lead bodies 142 is selected and the lead body connector 143 of the selected lead body is dragged and dropped onto one of the distal connectors 162 of the adaptor 160. Similarly, the other lead body 142 is selected and the lead body connector 143 of the selected lead body is dragged and dropped onto the other one of the distal connectors 162 of the adaptor 160. Thus, connections 166 between the lead bodies 142 and the adaptor 160 are defined, as shown in FIG. 8*b*. The proximal connector 164 of the adaptor 160 is selected, dragged, and dropped onto one of the output ports 154 of the IPG, thereby defining a connection 168 between the adaptor 160 and the output port 154. Thus, the connection between the lead bodies 142 and the output port 154 of the IPG includes connections 166 and 168.

Figure 9B:
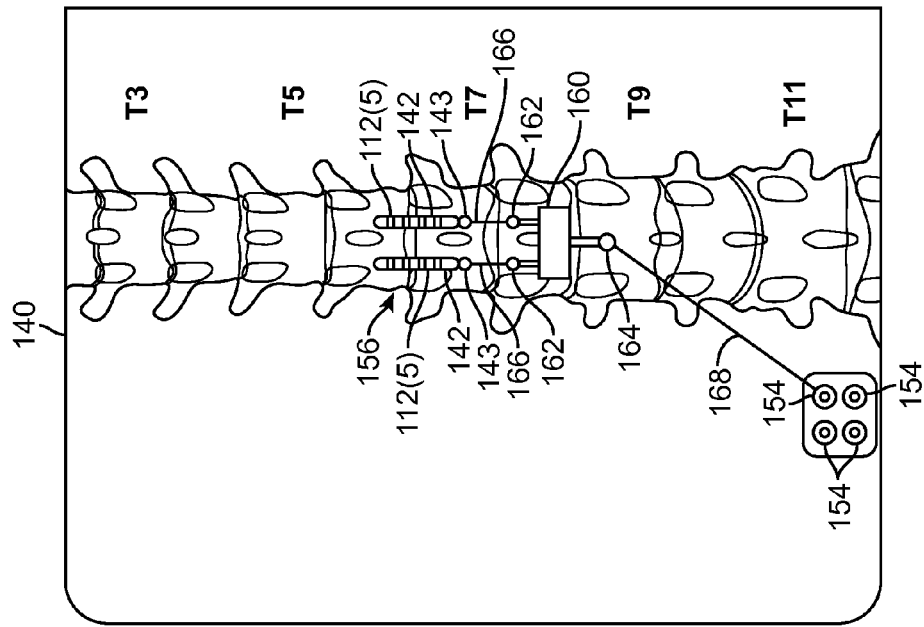
Figure 9A:
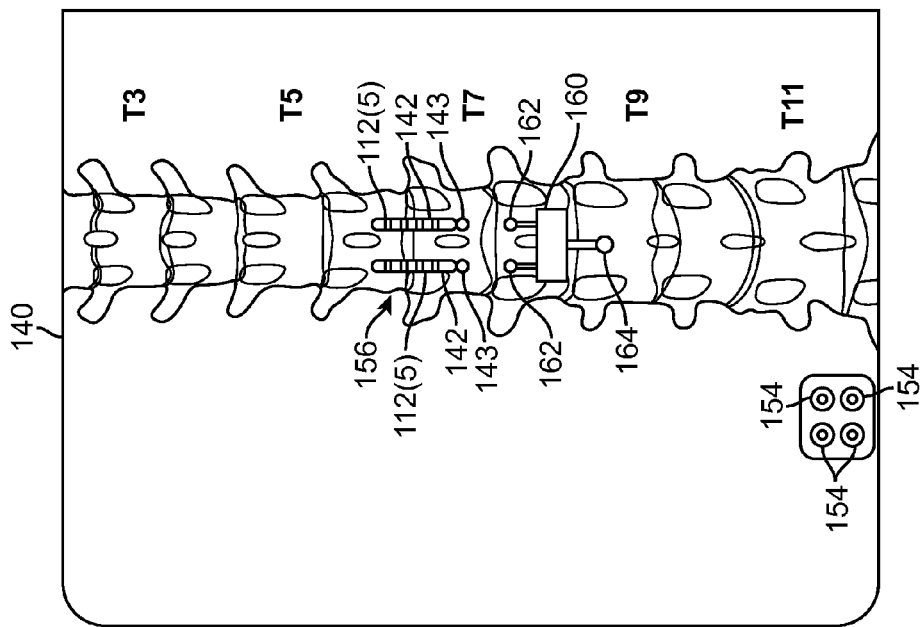

The lead bodies 142 in FIG. 9*a* are percutaneous leads 112(5) each having four electrodes. Each of the lead bodies 142 includes a lead body connector 143. An adaptor 160 is depicted in FIG. 9*a* as being disposed between the lead bodies 142 and the output ports 154 of the IPG. The side of the adaptor 160 facing the lead bodies 142 includes two distal connectors 162 configured for being coupled to the lead body connectors 143. The side of the adaptor 160 facing the output ports 154 of the IPG includes one proximal connector 164 configured for being coupled to one of the output ports 154 of the IPG. In this manner, the adaptor 160 is configured for coupling both of the lead bodies 142 to a single one of the output ports 154. In a method for defining the connection between the lead bodies 142 and one of the output ports 154, one of the lead bodies 142 is selected and the lead body connector 143 of the selected lead body is dragged and dropped onto one of the distal connectors 162 of the adaptor 160. Similarly, the other lead body 142 is selected and the lead body connector 143 of the selected lead body is dragged and dropped onto the other one of the distal connectors 162 of the adaptor 160. Thus, connections 166 between the lead bodies 142 and the adaptor 160 are defined, as shown in FIG. 9*b*. The proximal connector 164 of the adaptor 160 is selected, dragged, and dropped onto one of the output ports 154 of the IPG, thereby defining a connection 168 between the adaptor 160 and the output port 154. Thus, the connection between the lead bodies 142 and the output port 154 of the IPG includes connections 166 and 168.

Figure 10B:
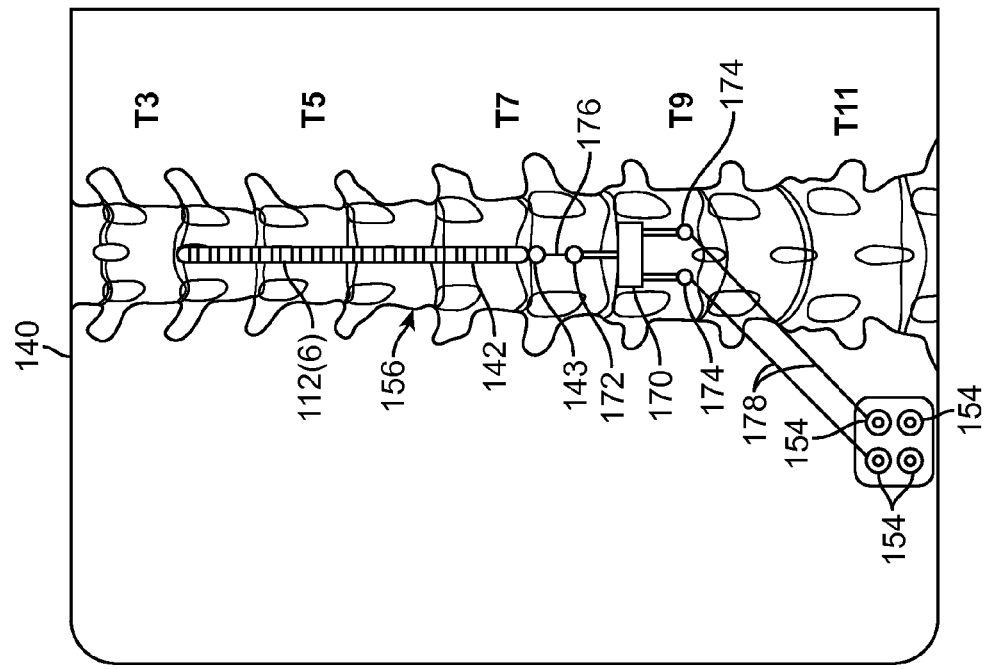
Figure 10A:
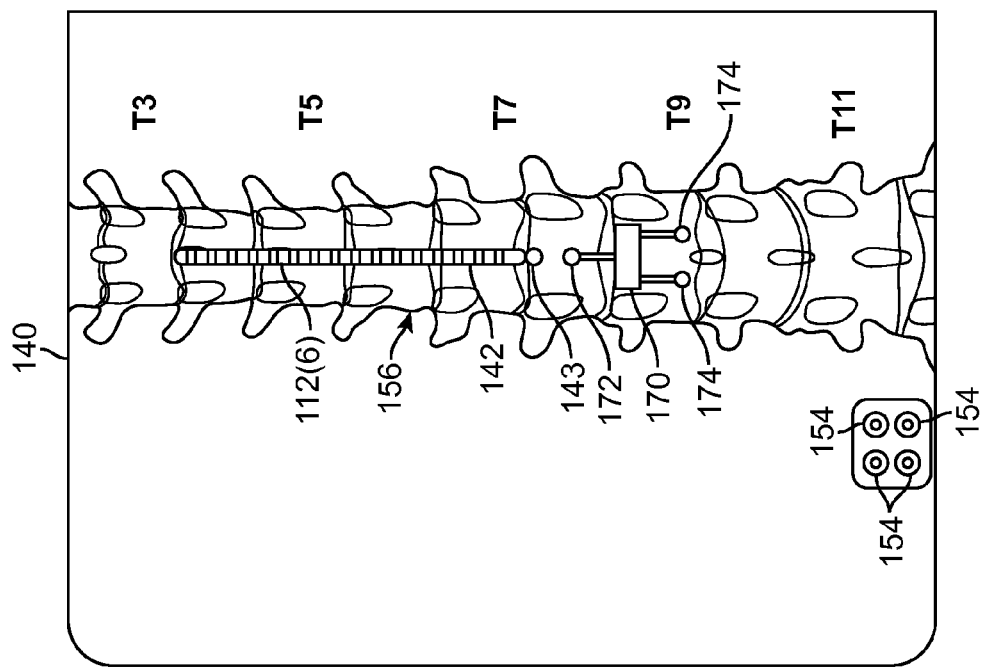

The lead body 142 in FIG. 10a is a percutaneous lead 112(6) having sixteen electrodes, all of which are coupled to the connector 143. A splitter 170 is depicted in FIG. 10a as being disposed between the lead body 142 and the output ports 154 of the IPG. The side of the splitter 170 facing the lead body 142 includes a distal connector 172 configured for being coupled to the lead body connector 143. The side of the splitter 170 facing the output ports 154 of the IPG includes two proximal connectors 174, each configured for being coupled to one of the output ports 154 of the IPG. In this manner, the splitter 170 is configured for coupling the lead body 142 to two of the output ports 154. In a method for defining the connection between the lead body 142 and the output ports 154, the lead body 142 is selected and the lead body connector 143 is dragged and dropped onto the distal connector 172 of the splitter 170, thereby defining a connection 176 between the lead body 142 and the splitter 170, as shown in FIG. 10b. One of the proximal connectors 174 of the splitter 170 is selected, dragged, and dropped onto one of the output ports 154 of the IPG. Similarly, the other proximal connection 174 of the splitter 170 is selected, dragged, and dropped onto another one of the output ports 154 of the IPG. Thus, connections 178 between the splitter 170 and the output ports 154 are defined. The connection between the lead body 142 and the output ports 154 of the IPG includes connections 176 and 178.

Although the foregoing technique has been described as being implemented in the CP 18, it should be noted that this technique may be alternatively or additionally implemented in the RC 16. Furthermore, although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. An external control device for selectively defining connections between a plurality of lead bodies, each coupled to at least one electrode, and a plurality of output ports of a neurostimulator, the external control device comprising:
   a user interface configured for receiving input from a user, and for displaying the lead bodies and the output ports of the neurostimulator; and
   control circuitry configured for, in response to input from the user, selecting a first one of the lead bodies, dragging a connector from the first lead body to a first one of the output ports of the neurostimulator, and dropping the connector onto the first output port of the neurostimulator, thereby defining a connection between the first lead body and the first output port of the neurostimulator.

2. The external control device of claim 1, wherein the control circuitry is further configured for, in response to input from the user, selecting a second one of the lead bodies, dragging a second connector from the second lead body to a second one of the output ports of the neurostimulator, and dropping the second connector onto the second output port of the neurostimulator, thereby defining a connection between the second lead body and the second output port of the neurostimulator.

3. The external control device of claim 1, wherein the control circuitry is further configured for verifying compatibility between the first lead body and the first output port of the neurostimulator.

4. The external control device of claim 1, wherein the control circuitry is configured for selecting the first lead body by coupling a pointing device to the first lead body, configured for dragging the connector by moving the pointing device, and configured for dropping the connector by decoupling the pointing device from the dragged connector.

5. The external control device of claim 1, wherein the user interface comprises one or more of a mouse, a trackball, a touchpad, and a joystick for receiving the input from the user.

6. The external control device of claim 1, wherein the user interface comprises a digitizer screen for receiving the input from the user.

7. The external control device of claim 1, wherein the control circuitry is further configured for, in response to additional input from the user, programming the neurostimulator with stimulation parameters corresponding to the at least one electrode to which the first lead body is coupled.

8. The external control device of claim 1, wherein the user interface is configured for displaying the connection between the first lead body and the first output port of the neurostimulator.

9. The external control device of claim 1, wherein the first lead body comprises one of a plurality of tails of a lead.

10. The external control device of claim 1, wherein the first lead body is a percutaneous lead.

11. A method for selectively defining connections between a plurality of lead bodies, each coupled to at least one electrode, and a plurality of output ports of a neurostimulator, the method comprising:
    displaying the lead bodies and the output ports of the neurostimulator;
    selecting a first one of the lead bodies;
    dragging a connector from the first lead body to a first one of the output ports of the neurostimulator; and
    dropping the connector onto the first output port of the neurostimulator, thereby defining a connection between the first lead body and the first output port of the neurostimulator.

12. The method of claim 11, further comprising verifying compatibility between the first lead body and the first output port of the neurostimulator.

13. The method of claim 11, further comprising:
    selecting a second one of the lead bodies;
    dragging a second connector from the second lead body to a second one of the output ports of the neurostimulator; and
    dropping the second connector onto the second output port of the neurostimulator, thereby defining a connection between the second lead body and the second output port of the neurostimulator.

14. The method of claim 11, further comprising programming the neurostimulator with stimulation parameters corresponding to the at least one electrode to which the first lead body is coupled.

15. The method of claim 11, wherein the first lead body comprises one of a plurality of tails of a lead.

16. The method of claim 11, wherein the first lead body comprises a percutaneous lead.

* * * * *